United States Patent [19]

Task et al.

[11] Patent Number: 5,712,709
[45] Date of Patent: Jan. 27, 1998

[54] HAZE AND TRANSMISSIVITY MEASUREMENTS

[75] Inventors: Harry Lee Task; Peter Marasco, both of Dayton, Ohio

[73] Assignee: The United States of America as represented by the Secretary of the Air Force, Washington, D.C.

[21] Appl. No.: 630,712

[22] Filed: Apr. 8, 1996

[51] Int. Cl.$^6$ .......................... G01N 21/17; G01N 21/88
[52] U.S. Cl. .......................... 356/432; 356/435; 356/239
[58] Field of Search .......................... 356/432, 435, 356/443, 237, 239

[56] References Cited

U.S. PATENT DOCUMENTS

| | | |
|---|---|---|
| 3,973,852 | 8/1976 | Moore et al. |
| 4,397,554 | 8/1983 | Genco et al. ................ 356/239 |
| 4,623,258 | 11/1986 | Task et al. ................ 356/432 |
| 4,637,072 | 1/1987 | Hellstrom ................ 455/607 |
| 4,687,338 | 8/1987 | Task et al. ................ 356/237 |
| 4,690,560 | 9/1987 | Coogan ................ 356/338 |
| 4,767,207 | 8/1988 | Takiguchi ................ 356/73.1 |
| 4,791,287 | 12/1988 | Fisher ................ 356/240 |
| 4,871,251 | 10/1989 | Preikschat et al. ................ 356/336 |
| 4,920,412 | 4/1990 | Gerdt et al. ................ 358/95 |
| 4,946,282 | 8/1990 | Task ................ 356/432 |
| 5,024,526 | 6/1991 | von Redwitz ................ 356/73 |
| 5,077,480 | 12/1991 | Traina ................ 250/575 |
| 5,101,113 | 3/1992 | Hirleman, Jr. et al. ................ 250/574 |
| 5,206,711 | 4/1993 | Berthold et al. ................ 356/436 |
| 5,218,417 | 6/1993 | Gay et al. ................ 356/237 |
| 5,298,750 | 3/1994 | Rericha ................ 250/338.5 |
| 5,416,594 | 5/1995 | Gross et al. ................ 356/237 |
| 5,426,501 | 6/1995 | Hokanson et al. ................ 356/335 |
| 5,477,328 | 12/1995 | Tokumaru ................ 356/437 |

*Primary Examiner*—F. L. Evans
*Attorney, Agent, or Firm*—Gerald B. Hollins; Thomas L. Kundert

[57] ABSTRACT

A portable and potentially computer-controlled aircraft windscreen or the like test arrangement for quantitative determination of haze and energy transmissivity characteristics in the windscreen material. The test arrangement includes two portable transducer enclosures which lend to convenient use in tested aircraft environments and provides optical assistance in achieving a desired alignment of these transducer enclosures prior to testing. Improved sensitivity over prior haze evaluation arrangements is achieved through use of this accurate alignment and through capture of a large fraction of a haze generated optical signal with an efficient transducer configuration. The testing arrangement also includes optical filtering capability and laser signal modulation assistance in excluding ambient illumination interference with measurement-related optical signals. A plurality of use environments are contemplated including military and non-military uses.

20 Claims, 2 Drawing Sheets

HAZE AND TRANSMISSIVITY MEASUREMENTS

RIGHTS OF THE GOVERNMENT

The invention described herein may be manufactured and used by or for the Government of the United States for all governmental purposes without the payment of any royalty.

BACKGROUND OF THE INVENTION

This invention concerns the field of measuring quantitatively the optical transmissivity and the haze or clouding present in transparent materials such as the plastic or glass used in vehicle windscreens.

In the field of military, commercial and private aircraft maintenance and in the government oversight of safety in these fields, there is need to quantify the degree of departure from being clear that a sample of normally transparent laminate material such as glass or plastic has incurred by its composition or through extended or abnormal usage. In the case of aircraft windscreens, for example, long exposure to bright sunlight and especially to the ultraviolet component in this sunlight-at higher altitudes and on the ground, results in a pronounced tendency for the transparent material of the structures to become clouded or hazed. Often this hazing is found to start in a local area of the structure and gradually spread from this area or a plurality of such areas until a sizable and functionally important part of the windscreen becomes impaired. Normal exposure of windscreen materials to airborne dust and other abrasive particles, the action of windscreen wiping devices and the ever-present human tendency to clean these windscreens by dry wiping and other damage-imparting procedures often adds microscopic scratching to this clouding or hazing tendency.

On the other hand, windscreen replacement expense, especially when the cost of labor and the cost of aircraft down time are considered, make it inappropriate to employ a repair or replacement procedure for windscreens which does not delay until significant vision impairment is present or foreseeably imminent. Clearly this is a judgment area which should not be left entirely to the variations of human perception i.e., an area wherein quantitative measurements are desirable.

Moreover, in both the maintenance field and in new aircraft procurement, haze is almost always one of the parameters specified for an aircraft windscreen. In general, the effect of haze is to scatter incoming light and cause a veiling luminance or brightness which results in a reduced contrast for objects viewed through the windscreen. This reduced contrast often translates to reduced visual performance on the part of a pilot or other windscreen users. Aircraft windscreen haze may be measured, for example, by way of ASTM procedure F943. Aircraft windscreen haze is frequently expressed as a percentage and is also often measured according to ASTM procedure D1003; or Federal Test Method No. 406, test procedure 3022. Each of these testing arrangements employs an optical integrating sphere, an arrangement which is improved upon in the present invention.

Systems for performing measurements of the haze and transmissivity nature are therefore known in the mensuration art. Many systems of this type are however, configured for laboratory use and involve large and inflexible equipment that is primarily capable of accurate and repeatable results. Systems of a somewhat related type are also configured for use in other haze measurement fields, fields as diverse as environmental pollution, climatic documentation, vehicle exhaust characterization, medical image evaluation and so on. There is also in existence a body of measurement systems which is devoted to a variety of other but related properties of windscreens-. Systems which measure image distortion, craze and backscatter characteristics of windscreens, for example. Generally, systems of all of these diverse types are not well adapted for use in the field, i.e. for use in an aircraft maintenance or inspection environment.

There is perceived to be needed in the art a convenient and easily field accomplished quantitative test for transparency haze, a test which can be used by aircraft owners and maintenance personnel as well as by government and insurer and other third party interested persons. Moreover, this apparatus is desirably of such nature that its utility extends outside the aircraft or vehicle field and lends to use in a variety of repair and maintenance environments and to environments such as laboratory investigations, which are outside the maintenance field. The present invention is believed to provide this capability.

The U.S. patent art indicates the presence of inventive activity in the area of windscreen haze measurement; included in this art are a pair of patents issued to H. L. Task et al., (H. L. Task is one of the present inventors), U.S. Pat. Nos. 4,623,258 and 4,687,338. These patents disclose haze determinations requiring the measurement of precise angles, multiple luminance values and the accomplishment of a mathematical calculation in the case of the '258 patent and the comparison of device under test and worst case samples plus a related mathematical calculation in the case of the '338 patent. Each of these arrangements is therefore believed to be of only general interest with respect to the present invention.

A patent application which appears to be of some interest with respect to the present invention also involves inventor H. L. Task and is concerned with the measurement of a backscatter component of windscreen haze, a measurement accomplished using a large area illumination source. This application is titled "Backscatter Haze Measurement Using a Distributed Light Source" and has been assigned the U.S. Patent and Trademark Office Ser. No. of 08/416,600. Among other differences, the nature of the light source and the use of backscatter components are believed to distinguish the present invention from the teachings of the '600 application.

Another patent which appears to be of interest with respect to the present invention, U.S. Pat. No. 4,946,282, additionally involves inventor H. L. Task and is also concerned with measurement of windscreen transmissivity. In the '282 patent a diffused light source and a relatively small area photodetector, of selected surface area size with respect to an energy communicating aperture of the apparatus, are disposed on opposite sides of the measured windscreen material. The nature of the employed light source and detector are alone believed to distinguish the present invention from the teachings of the '282 patent.

Measurement of optical transmissivity is also disclosed the U.S. Pat. No. 5,077,480 of Traina; this patent is, however, concerned with a gaseous sample and is therefore believed limited to being of background interest with respect to the present invention.

In addition, the measurement of transmissivity and other phenomena in the atmosphere is disclosed in a series of U.S. Patents which includes the documents numbered U.S. Pat. Nos. 3,973,852; 4,920,412; 5,024,526; 5,298,750; and 5,477,328. Concern with an atmospheric sample is believed to make these documents of lesser and background interest with respect to the present invention.

Additionally, the measurement of particle sizes and quantities in a fluid medium is disclosed a series of U.S. Patents which includes the documents numbered U.S. Pat. Nos. 4,871,251; 5,101,113; and 5,426,501. The measurement of additional fluid properties such as turbidity and opacity is also disclosed in the U.S. Pat. Nos. 4,690,560 and 5,206,711. The concern with particle properties and fluids in these documents is believed to also make their disclosure of lesser interest with respect to the present invention.

Moreover, the measurement of dispersion and other phenomena in an optical fiber is disclosed in a series of U.S. Patents which includes the documents numbered U.S. Pat. Nos. 4,637,072 and 4,767,207. Concern with the properties of an optical fiber is believed to make these documents also of lesser interest with respect to the present invention.

SUMMARY OF THE INVENTION

The present invention measures aircraft windscreen transparency haze and transmissivity by using a large area distributed array of photodetectors to obtain measurement input signals of an improved signal-to-noise ratio. The invention uses a modulated laser diode as a light source that is disposed on one side of the windscreen and employs a cavity array of large photo detectors on the other windscreen side to capture and detect light scattered by windscreen haze. Unscattered light passes through a hole in the rear of the detector cavity to avoid its measurement and to enable visual alignment of the light source and detector. This unscattered light is also captured by a reference detector to measure windscreen transmissivity. To reduce noise, the detector circuit is tuned to a preset frequency at which the laser diode's signal is modulated.

It is an object of the present invention therefore, to provide a simplified windscreen haze measurement arrangement which lends well to use under field conditions but is nevertheless of sufficient accuracy to be of interest in performing precision measurements.

It is another object of the invention to provide a simplified windscreen haze measurement arrangement which also provides measurement of windscreen optical transmissivity.

It is another object of the invention to provide a simplified windscreen haze measurement arrangement which operates with improved accuracy and reliability through achieving increased signal-to-noise to noise ratio in the optical detector apparatus.

It is another object of the invention to provide a windscreen haze measurement arrangement which employs a plurality of signal-to-noise ratio enhancing techniques.

It is another object of the invention to provide a windscreen haze measurement arrangement which employs both optical bandpass filtering and optical signal modulation distinctions over ambient noise interference.

It is another object of the invention to provide a simplified windscreen haze measurement arrangement in which already generated optical signals can be employed for optical alignment of measurement apparatus components.

It is another object of the invention to provide a simplified windscreen haze measurement system which includes system components of a limited physical size, a size usable in the confines of a small aircraft.

It is another object of the invention to provide a simplified windscreen haze measurement arrangement which lends to use outside the vehicle, aircraft and aircraft windscreen measurement arts.

It is another object of the invention to provide a windscreen haze and transmissivity measurement apparatus which can be embodied with the controlling and computational assistance of a digital computer.

Additional objects and features of the invention will be understood from the following description and claims and the accompanying drawings.

These and other objects of the invention are achieved by the method of measuring haze in a transparency comprising the steps of:

positioning an optical energy source and optical energy receiver in physically aligned optical signal communicating positions on opposing sides of a to-be-measured thickness portion of said transparency;

communicating collimated optical energy from a semiconductor laser electrical-to-optical transducer located within said optical energy source through said to-be-measured thickness of said transparency to a scattered-received-signal-energized first electrical signal generating distributed first optical-to-electrical transducer element located in said optical energy receiver;

directing collimated optical energy from said semiconductor laser electrical to optical transducer located within said optical energy source through said to-be-measured thickness of said transparency to a collimated optical energy-energized second electrical signal generating second optical to electrical transducer element located in said optical energy receiver;

processing said first and second electrical signals to generate a third electrical signal representing a mathematical summation of said first and second electrical signal magnitudes and total optical energy passing through said to-be-measured thickness portion of said transparency; and forming from said first electrical signal and said third electrical signal a tested transparency haze-related fourth quotient signal representing said first electrical signal magnitude mathematically divided by said third electrical signal magnitude.

DETAILED DESCRIPTION

Figure 1:
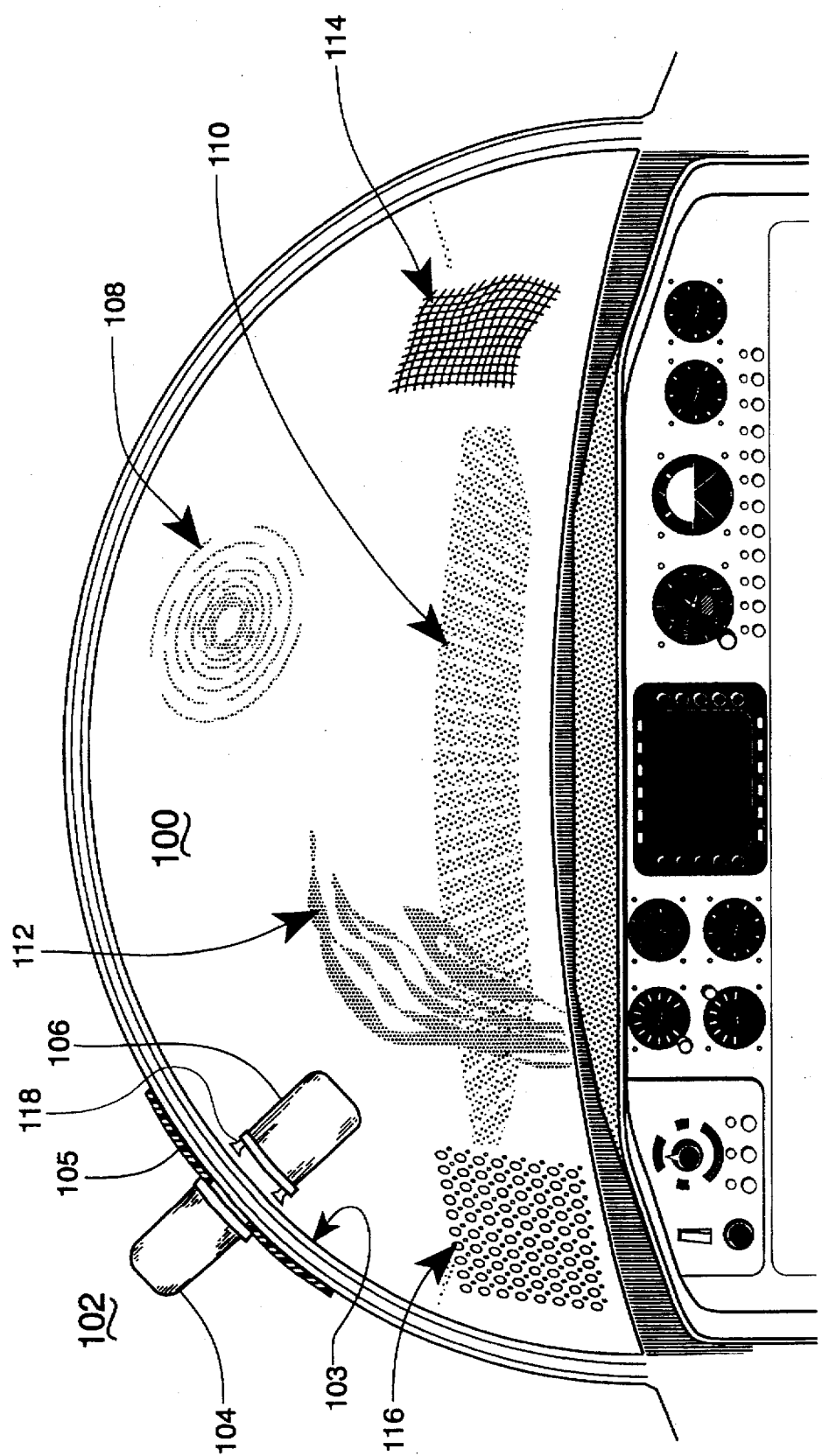
FIG. 1 shows a physical arrangement of apparatus according to the invention in a windscreen haze evaluation environment.

FIG. 1 in the drawings shows an overall perspective view of apparatus which may be used to embody the present invention as this apparatus is in a deployed for use condition. In the FIG. 1 drawing, there is shown a representative aircraft windscreen 100, a windscreen of the contoured laminated plastic type such as is used on modem tactical aircraft, with this windscreen being in a simulated cockpit mounted condition. The FIG. 1 windscreen 100 is shown to be undergoing a through-the-windscreen-material light transmission examination by an optical sensing apparatus which is generally indicated at 102, an apparatus which is comprised of a transmitter element 104 and a receiver element 106. The optical transmitter element 104 is, for example, shown to be located on the exterior surface of the windscreen 100 in the region of examination 103 and the optical receiver 106, shown located adjacent the interior surface of the windscreen; these locations can generally be reversed for purposes of the present invention, however. The optical transmitter element 104 and optical receiver element 106 of FIG. 1 are presumed to be tether-connected to additional apparatus. This will become more apparent in connection with the FIG. 2 drawing; however, these additional appendages are omitted in FIG. 1 for drawing simplicity.

Figure 2:
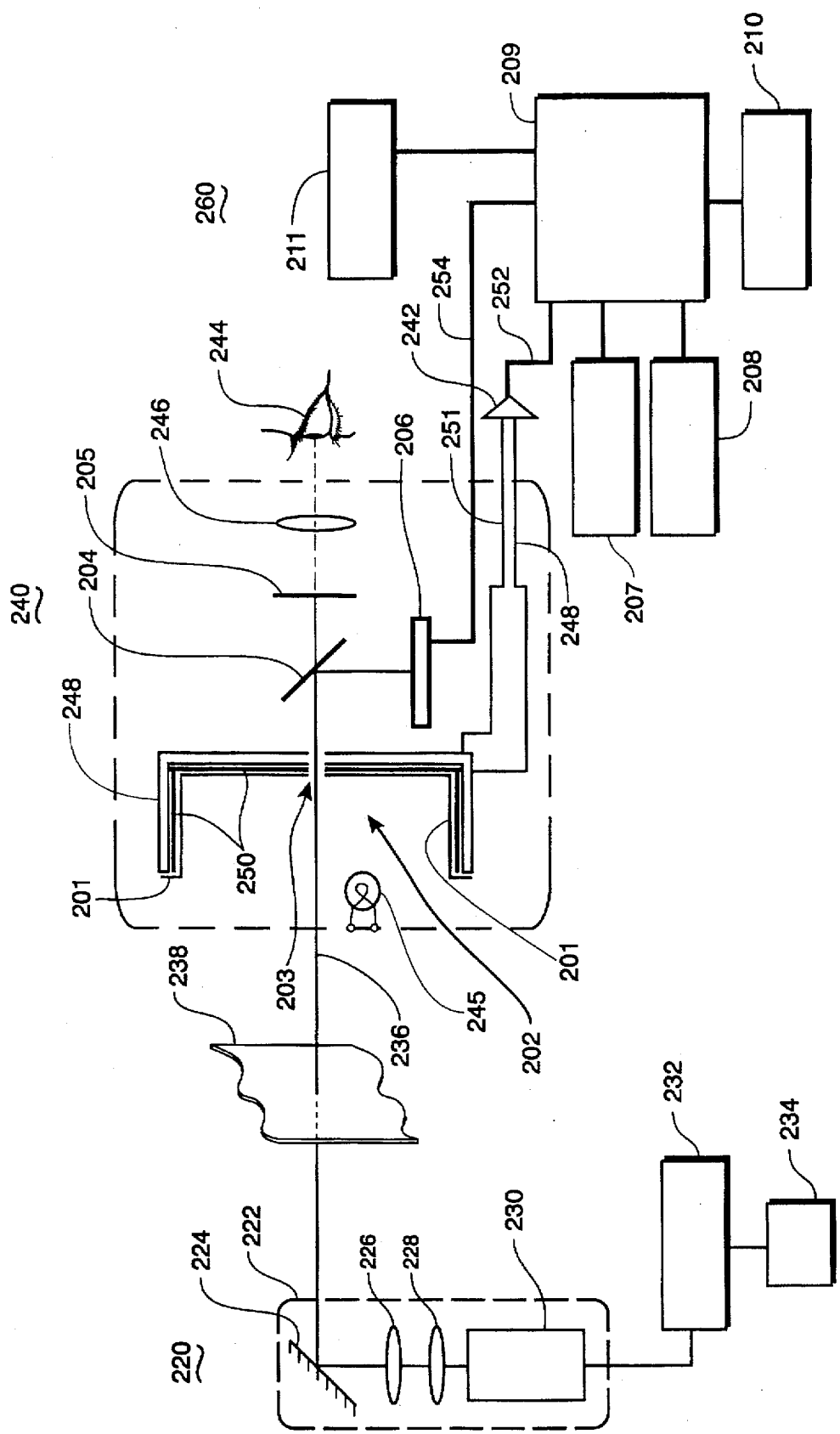
FIG. 2 shows a functional block diagram of apparatus which may be used to embody the invention.

Before embarking into a discussion of the optical sensing apparatus 102 in its more detailed FIG. 2 form, it may be helpful to understand that the windscreens used on modern aircraft, particularly windscreens for military aircraft, have evolved from the glass-based structures used in high altitude aircraft designed up to the 1960's into the contoured, laminated plastic structure shown in FIG. 1. This structure, which especially finds use on low level aircraft designed more recently, is often fabricated as a multiple layered plastic assembly employing, for example, polycarbonate materials, and affords a significant but certainly not total degree of impact protection for the aircraft pilot. Such protection is especially significant for lower level aircraft operation where the danger of bird strike and other impact is present.

Although flat-plane, glass-based windscreen arrangements are not free of visibility problems, it is easy to appreciate that FIG. 1 type curved and laminate structures frequently bring on several vision problems which are especially difficult to fully resolve. These problems are in addition to the fundamental fact that a relatively thick assembly of plastic layers is in most instances simply not as clear as a thin layer of glass material. Several of these additional problems are represented in the FIG. 1 drawing as a matter of background interest with respect to the present invention.

A first of these contoured and laminated windscreen characteristics provides the image distortion represented at 114 in the FIG. 1 drawing; the image shown in this instance being a pilot's view of a perfectly square grid pattern when this pattern is transmitted through more curving portions of a FIG. 1 type windscreen. A second of these characteristics, an ability to generate rainbow-like interference patterns, is represented at 112 in FIG. 1. Such patterns, especially when generated from bright sunlight, can substantially obscure vision through a sizable area of a windscreen.

Another of these windscreen defect characteristics, a tendency to reproduce multiple output images of a single input object, is represented at 116 in FIG. 1; the small lighter density dots in the pattern at 116 are, of course, absent in the input image and are generated by optical properties of the windscreen 100. Additional visibility impairments which can occur in a windscreen include crazing effects, reflections (often from internal parts of the aircraft and represented at 110 in FIG. 1), angular distortion, and haze effects. The crazing, reflections and angular distortion characteristics are not shown in the FIG. 1 drawing since they are difficult to represent in a non-photographic environment. The latter of these characteristics, the tendency of a windscreen to be or become hazed, is of special interest with respect to the present invention and is represented to the best degree possible, within a drawing, at 108 in FIG. 1. Another haze area, although not represented in FIG. 1, is similar to the representation at 108 and is under consideration in the region 103 by the optical sensing apparatus at 102 in FIG. 1.

Two of the FIG. 1 defects which are especially important criteria for judging aircraft windscreen condition are therefore haze and its related criteria of transmissivity. Haze changes dramatically as a windscreen ages, thereby affecting its transmissivity. Haze is a major reason for many costly, time consuming windscreen replacements. Reliably measuring both haze and transmissivity has, heretofore, been primarily confined to the laboratory and has required that the windscreen be removed from an aircraft merely for such testing, an option unacceptable to operational military units, civilian airlines, and private pilots alike. The presently used systems for measuring haze of windscreens while they are located on the aircraft have also been plagued by problems such as system component size, weight, sensitivity to alignment, and susceptibility to stray light. These and other problems cause such systems to be inaccurate and/or difficult to use.

Turning now to FIG. 2 in the drawings, this drawing shows a block diagram and schematic representation of a system which may be used to quantitatively evaluate several of the FIG. 1 related windscreen defects, a system which is however, especially well suited to evaluation of the haze characteristic and also to determining the degree of clearness or the optical transmissivity of materials used in structures such as the FIG. 1 windscreen. It is significant to note that the system represented in FIG. 2 is fully portable and well adapted to non laboratory use and use in environments found at any level of aircraft maintenance.

The FIG. 2 system is, of course, not limited to aircraft related usage and may find application in a variety of other fields. In this regard the word "transparency", which is used frequently in the specification and claims of this document, is intended to identify any transparent material disposed in any physical configuration and is therefore employed as a matter of convenience rather than as a limitation. In the transportation vehicle art, it is intended that the invention find application in connection with boat windows, hovercraft windows, motorcycle windscreens, train and subway windscreens, for examples. It is also intended that the invention be usable in other non transportation-related "transparencies" such as in the quantitative evaluation of plate glass and plastic materials in sheet or other forms.

The FIG. 2 system is made up of three primary parts, an optical source apparatus 220, a detector head assembly 240 and a recording and analysis-controller apparatus 260. Light from a laser emitter in the optical source apparatus 220 originates from a modest power, class 3a red laser diode, indicated at 230, and is modulated, preferably by electrical circuitry which controls energy flow to this laser diode 230, the circuitry indicated at 232. This circuitry preferably receives sinusoidal waveform or other modulation from the source 234. Optical energy from the laser diode 230 is passed through lenses 226 and 228 to correct for the astigmatism naturally present in a laser diode's output and in order to focus this energy through the aperture 203 at the rear of the detector head assembly and onto the diffusing reticule 205 and the reference detector 206.

The test windscreen material is represented in cross section at 238 in FIG. 1. The gaps between windscreen material 238 and the optical source apparatus 220 and detector head assembly 240 are shown to be relatively large for drawing convenience in FIG. 1; actually close spacing between the detector head assembly 240 and the material 238 is desirable in order to capture as much of the diffused optical energy emerging from the material 238 as possible. In a related manner, close spacing between the optical source apparatus 220 and the material 258 is desired in order to exclude as much ambient light from the detector head assembly 240 as possible.

To minimize the overall size of the enclosure 222 for the optical source 220 and to make it more convenient in limited space locations, a turning mirror 224 is used to change the direction of the source output beam 236 by ninety degrees. Mirror 224, lenses 226 and 228, and laser diode 230 are then contained in the enclosure 222 which has a window or exit aperture in one side to allow emergence of beam 236. This exit aperture is preferably surrounded by rubber pads or "feet" to assist in enclosure 222 alignment retention on a windscreen 100 surface and to protect this windscreen surface from scratching. The detector head assembly 240 is also preferably provided with small rubber "feet", as represented at 118 in FIG. 1, or some equivalent arrangement to prevent scratching a windscreen under test and to assist in retaining the assembly 240 in a selected position of alignment with the optical source apparatus 220 notwithstanding small vibrations and the like.

To keep the laser emitter enclosure 222 small, the power supply 232, modulating circuitry, and batteries or other energy supply arrangement may be located in a separate package and connected by a cable to the enclosure 222. A large area light baffle, as appears at 105 in FIG. 1, may be made of some soft, flexible, non-reflecting material, such as rubber and disposed on one side of the windscreen 100 to reduce the mount of stray light entering the detector head assembly 240.

The detector head assembly 240 includes a detector cavity 202 having a series of optical to electrical transducer elements arranged in a closed end cylindrical or closed end n-sided polygon configuration; n here can have any desired value above 3. The n-sided polygon arrangement is particularly useful where curved transducer elements are not available. The cylindrical or n-sided physical support element portion of the detector cavity 202 is indicated at 248 in FIG. 1 and the large area optical to electrical transducer elements which are received around the interior of this support element 248 are indicated at 250. These transducer elements may be of, for example, the silicon solar cell type, possibly the amorphous silicon solar cell type, and are disposed over the lateral and end interior surface portions of the detector cavity 202 in order to capture as much as possible of the randomly oriented optical energy diverted from the beam 236 by windscreen haze or other FIG. 1 defects. In instances wherein a satisfactory parallel or series direct electrical interconnection of the several discrete transducer elements covering the interior of the detector cavity 202 cannot be arranged, a summing operational amplifier as indicated at 242 may be employed to generate, from the path 248 detector lateral surface and the path 251 detector end surface output signals, a path 254 single output signal representing total optical energy received on the interior surface of the detector cavity 202.

At the back end of the detector cavity 202, a small aperture 203 is provided to allow the unscattered portion of the laser beam 236 to escape without energizing the detector cavity 202 solar cells. This unscattered light is divided by a beam splitter 204 as it emerges from the aperture 203, sending some of the energy to a reference detector 206 and the remainder to an alignment screen or reticule 205. The reticule 205 is preferably provided with proper alignment-indicating markings such as an army of concentric circles in order that an observer, represented by the eye 244, can discern when the optical source apparatus 220 and the detector head assembly 240 are correctly aligned on opposing sides of the windscreen 100. This alignment indicates, of course, that the beam 236 is directed through a central part of the aperture 203 and not impinging on the transducer solar cells of the detector cavity 202 where it would be interpreted as haze-produced random orientation optical energy.

Use of the large surface area and the optical energy capturing shape of the detector cavity 202 is in fact a significant aspect of the present invention. The transducing of a large portion of the haze-dispersed optical energy of the beam 236 resulting from this large surface area provides a greater signal level and better signal-to-noise ratio in the electrical output signal of path 252 than previous arrangements used for haze evaluation. In particular, the FIG. 2 large surface area transducer utilizes a significantly greater portion of the haze diverted energy of the beam 236 than arrangements which rely on the properties of an integrating spherical member and the small detector element usually associated therewith.

An optical bandpass filter 201, selected to pass the spectral wavelength of the laser diode, may be placed over the surface of the transducers in the detector cavity 202 to exclude unwanted stray light from the transducers and to further improve the signal-to-noise ratio of the path 252 signal. It is additionally desirable to provide an electrically selective filter in the path 252 or elsewhere in the electrical signal paths of FIG. 2 in order to further attenuate signals not impressed with the modulation frequency and waveform supplied at 234, e.g., to additionally exclude ambient light and other noise signal components.

Signals from the transducer 206, the coherent beam or reference transducer, and signals from the transducer of the detector cavity 202 are communicated via the paths 254 and 252 respectively to the recording and analysis-controller apparatus 260 where mathematical processing, data storage, and data display functions, for example, are accomplished. Many of the functions of the recording and analysis-controller apparatus 260 can be conveniently accomplished in the block 209 by a digital computer provided with analog signal input capability, a capability which includes an analog to digital converter, for example. Alternately, a dedicated hardware embodiment of the block 209 functions can be employed. As indicated at 207, 208 and 211 the set-up and power supply needs of the computer or the dedicated hardware may be provided in conventional manual-input inclusive ways. A lock-in or sample and hold amplifier may be used for precision enhancement to sort noise from the modulated laser signal in the block 209 processing. Calibration, haze, and transmissivity information may be displayed on separate Liquid Crystal Displays, (LCDs), as indicated at 210 in the recording and analysis-controller apparatus 260.

Incorporated in the signal processing capability provided in block 209 is an ability to perform mathematical manipulations on the signals arriving on paths 252 and 254. This manipulation includes the ability to generate a mathematical sum of the path 252 and 254 signals i.e., to generate a signal representing all of the optical energy communicated through the material 238 of the device under test windscreen including its haze-dispersed and non haze-dispersed components. One output signal of the FIG. 2 apparatus, an output signal representing the incurred degree of haze degradation of the windscreen material 238, is obtained by mathematically dividing the haze related component signal from path 252 by this path 252 and 254 mathematical sum signal. This division operation may be performed by analog or digital means in the block 209 processing. In the latter digital instance, the division may additionally be performed by software processing or by dedicated hardware processing arrangements which are each known in the art. Similar mathematical processing of the path 254 signal, i.e., division of this signal's magnitude by the mathematical sum signal, may be used to obtain a measure of transmissivity for the windscreen material 238, since the path 254 signal represents collimated optical energy which has passed unaffected through the windscreen material.

Operational use of the FIG. 1 and FIG. 2 disclosed apparatus is straightforward. First, the detector cavity 202 of the detector head assembly 240 is calibrated against an internal calibration light source, represented at 245. This ensures that the detector lateral side and end surface transducers yield a predetermined amount of signal (as established in selecting the input gains of amplifier 242, for example) when equal inputs from the laser 230 are incident on these surfaces. Then the optical source apparatus 220 is placed on one side of the windscreen to be tested and activated so that the beam 236 passes through a selected cross section of the windscreen material and is fairly perpendicular to the windscreen's surface. This perpendicular alignment will be facilitated by making sure that the small rubber feet touch the windscreen. Then the detector head is placed in contact with the opposed surface of the windscreen, supported by its rubber feet, and positioned so that the unscattered beam emerges from the aperture 203 in a centered condition on the alignment reticule 205. A measurement can be taken with the press of a button, displaying haze and transmissivity values on LCD readouts in the recording and analysis-controller apparatus 260.

The system disclosed herein is believed to be the first haze measuring device to use an all solid-state detector array. This detector arrangement eliminates the need for an integrating sphere, a source of bulk for current haze measuring devices. The presently disclosed large solid-state detectors are more sensitive to small signals than previous integrating sphere based devices because of the elimination of integrating sphere reflection losses, thus making the FIG. 1 and FIG. 2 apparatus more sensitive to small amounts of haze. The disclosed apparatus is also capable of testing transparencies while they are still on an aircraft or other vehicle and permits the simultaneous and direct measurement of both transparency haze and transmissivity.

The discrete wavelength of the herein disclosed-laser source allows for use of bandpass filters to significantly reduce measurement inaccuracies due to stray light noise. The laser source also provides greater power per unit area than the incandescent source which is common to other haze measuring devices, thereby adding to the system's sensitivity to windscreen haze. The system's small size and light weight permits its convenient use by a single operator and the small beam size allows an operator to measure small areas on the windscreen. A plurality of these small area measurements will yield an accurate haze and transmissivity profile across an aircraft transparency.

While the apparatus and method herein described constitute a preferred embodiment of the invention, it is to be understood that the invention is not limited to this precise form of apparatus or method and that changes may be made therein without departing from the scope of the invention which is defined in the appended claims.

What is claimed is:

1. The method of measuring haze in a transparency comprising the steps of:

positioning an optical energy source and optical energy receiver in physically aligned optical signal communicating positions on opposing sides of a to-be-measured thickness portion of said transparency;

communicating collimated optical energy from a semiconductor laser electrical-to-optical transducer located within said optical energy source through said to-be-measured thickness of said transparency to a scattered-received-signal-energized first electrical signal generating distributed first optical-to-electrical transducer element located in said optical energy receiver;

directing collimated optical energy from said semiconductor laser electrical-to-optical transducer located within said optical energy source through said to-be-measured thickness of said transparency to a collimated optical energy-energized second electrical signal generating second optical-to-electrical transducer element located in said optical energy receiver;

processing said first and second electrical signals to generate a third electrical signal representing a mathematical summation of said first and second electrical signal magnitudes and total optical energy passing through said to-be-measured thickness portion of said transparency; and forming from said first electrical signal and said third electrical signal a tested transparency haze-related fourth quotient signal representing said first electrical signal magnitude mathematically divided by said third electrical signal magnitude.

2. The method of measuring transparency degradation of claim 1 further including the step of:

forming from said second electrical signal and said third electrical signal a tested transparency transmissivity-related fifth quotient signal representing a first electrical signal magnitude mathematically divided by a third electrical signal magnitude.

3. The method of measuring transparency degradation of claim 1 further including the step of generating said collimated optical energy by transducing electrical energy into optical energy of a selected spectral frequency content in a laser diode element.

4. The method of measuring transparency degradation of claim 1 further including the step of disposing said first electrical signal generating distributed first optical to electrical transducer element as an internal surface covered closed end geometric polygon.

5. The method of measuring transparency degradation of claim 1 wherein said step of positioning an optical energy source and an optical energy receiver in physically aligned optical signal communicating positions includes manually viewing an image formed by a transparency-transmitted beam component of said collimated optical energy on an optimum alignment-indicating reticule element.

6. The method of measuring transparency degradation of claim 1 further including the step of generating optical energy within said optical energy source by transducing modulated electrical energy into modulated optical energy in a semiconductor laser diode element.

7. The method of measuring transparency degradation of claim 1 further including the step of positioning said optical energy source and said optical energy receiver in a plurality of different physically aligned optical signal communicating positions on said transparency.

8. Transparency evaluation apparatus comprising the combination of:

a portable source of collimated optical energy disposable on one surface of a transparency device under test;

a portable collimated optical energy receiver disposable on an opposing surface of a transparency device under test and in optical communication through material of said transparency with said portable source of collimated optical energy;

collimated optical beam alignment means located in said portable collimated optical energy receiver for optically aligning said portable source of collimated optical energy with said portable collimated optical energy receiver through said transparency;

first optical-to-electrical energy transducer means located in said portable collimated optical energy receiver for generating a first electrical signal representative of a magnitude of a collimated optical signal received through said transparency material;

second optical-to-electrical energy transducer means located in said portable collimated optical energy receiver for generating a second electrical signal representing a magnitude of a diffused optical signal received through said transparency material;

said second optical-to-electrical energy transducer means including a large surface optical-to-electrical transducer element of semi-closed geometric configuration disposed in capturing optical communication with said diffused transparency material-communicated optical signal; and signal processing means for generating an electrical signal representing one of an transparency haze-related quotient of said first electrical signal magnitude divided by a magnitude summation of said first and second electrical signals and an transparency transmissivity-related quotient of said second electrical signal magnitude divided by said magnitude summation of said first and second electrical signals.

9. The transparency evaluation apparatus of claim 8 wherein said collimated optical beam alignment means for optically aligning said portable source of collimated optical energy with said portable collimated optical energy receiver through said transparency comprises;

optical viewing means for manually observing an image representation of said collimated optical beam's path within said portable collimated optical energy receiver.

10. The transparency evaluation apparatus of claim 9 wherein said optical viewing means comprises a manually observable reticule element.

11. The transparency evaluation apparatus of claim 9 wherein said manually observable reticule element is disposed along an optical path communicating through a central portion aperture of said semi-closed geometric configuration second optical to electrical energy transducer means large surface area optical-to-electrical transducer element.

12. The transparency evaluation apparatus of claim 9 wherein said source of collimated optical energy includes a laser diode transducer element.

13. The transparency evaluation apparatus of claim 12 further including:

means for modulating an optical output signal of said laser diode with a selected modulation waveform; and electrical wave filter means connected with one of said first and second electrical output signals for excluding noise signals not modulated with said selected waveform.

14. The transparency evaluation apparatus of claim 8 wherein said large surface area optical-to-electrical transducer element of semi-closed geometric configuration comprises a geometric shape of one of an end-closed right circular cylinder and an end-closed n-sided polygon.

15. The transparency evaluation apparatus of claim 14 wherein said large surface area optical-to-electrical transducer element of semi-closed geometric configuration further includes a collimated optical signal communicating aperture located in an end closure portion of said right circular cylinder and said end-closed n-sided polygon.

16. The transparency evaluation apparatus of claim 15 wherein said collimated optical beam alignment means comprises said collimated optical signal communicating aperture and an eye viewable reticule member each disposed along a communication path of said collimated optical signal in said portable collimated optical energy receiver element.

17. The transparency evaluation apparatus of claim 8 wherein said portable collimated optical energy receiver element further includes an optical bandpass filter element of bandpass characteristics coincident with an optical output of an electrical-to-optical transducer element disposed in said source of collimated optical energy.

18. The transparency evaluation apparatus of claim 12 wherein said source of collimated optical energy includes a laser diode transducer element and lens means for astigmatism correction in the optical output signal of said laser diode transducer element.

19. Aircraft windscreen transparency evaluation apparatus comprising the combination of:

an electrically modulated laser diode-inclusive portable source of a collimated optical energy beam disposable on one surface of an aircraft windscreen transparency device under test;

an optical bandpass filter element-inclusive portable collimated optical energy receiver disposable on an opposing surface of said aircraft windscreen transparency device under test and in optical communication through said aircraft windscreen transparency material with said portable source of collimated optical energy optical beam;

collimated optical beam alignment means located in said portable collimated optical energy receiver for optically aligning said portable source of collimated optical energy with said portable collimated optical energy receiver through said aircraft windscreen transparency;

said collimated optical beam alignment means comprising manually viewable reticule element-inclusive optical viewing means for manually observing an image representation of said collimated optical beam's path within said portable collimated optical energy receiver;

first optical-to-electrical energy transducer means located in said portable collimated optical energy receiver for generating a first electrical signal representative of a magnitude of a collimated optical signal received through said aircraft windscreen transparency material;

second optical-to-electrical energy transducer means located in said portable collimated optical energy receiver for generating a second electrical signal representing a magnitude of a diffused optical signal received through said aircraft windscreen transparency material;

said second optical-to-electrical energy transducer means including a large surface area optical-to-electrical transducer element of semi-closed geometric configuration disposed in capturing optical communication with said diffused aircraft windscreen transparency material-communicated optical signal; and signal processing means for generating an electrical signal representing one of an aircraft windscreen transparency haze-related quotient of said first electrical signal magnitude divided by a magnitude summation of said first and second electrical signals and an aircraft windscreen transparency transmissivity-related quotient of said second electrical signal magnitude divided by said magnitude summation of said first and second electrical signals.

20. The method of measuring haze in an aircraft windscreen transparency comprising the steps of:

positioning an optical energy source and optical energy receiver in physically aligned optical signal communicating positions on opposing sides of a to-be-measured thickness portion of said aircraft windscreen transparency;

communicating collimated modulated optical energy from a semiconductor laser electrical-to-optical transducer located within said optical energy source through said to-be-measured thickness of said aircraft windscreen transparency to a scattered-received-signal-energized first electrical signal generating distributed first optical-to-electrical transducer element located in said optical energy receiver;

directing collimated optical energy from said semiconductor laser electrical-to-optical transducer located within said optical energy source through said to-be-measured thickness of said aircraft windscreen transparency to a beam of collimated optical energy-energized second electrical signal generating second optical-to-electrical transducer element located in said optical energy receiver;

processing said first and second electrical signals to generate a third electrical signal representing a mathematical summation of said first and second electrical signal magnitudes and total optical energy passing through said to-be-measured thickness portion of said aircraft windscreen transparency; and forming from said first electrical signal and said third electrical signal a tested windscreen haze-related fourth quotient signal representing said first electrical signal magnitude mathematically divided by said third electrical signal magnitude.

* * * * *